(12) United States Patent
Lurie et al.

(10) Patent No.: US 6,935,336 B2
(45) Date of Patent: *Aug. 30, 2005

(54) SYSTEMS AND METHODS TO FACILITATE THE DELIVERY OF DRUGS

(75) Inventors: Keith G. Lurie, Minneapolis, MN (US); Wolfgang Voelckel, Telfs (AT)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/920,678

(22) Filed: Aug. 17, 2004

(65) Prior Publication Data

US 2005/0016541 A1 Jan. 27, 2005

Related U.S. Application Data

(63) Continuation of application No. 09/967,029, filed on Sep. 28, 2001, now Pat. No. 6,776,156.

(51) Int. Cl.[7] ............................................. A61M 16/00
(52) U.S. Cl. .............................. 128/200.24; 128/205.24
(58) Field of Search ..................... 128/202.28, 202.29, 128/203.11, 205.24, 204.18, 204.26, 200.24

(56) References Cited

U.S. PATENT DOCUMENTS

| | | |
|---|---|---|
| 2,774,346 A | 12/1956 | Halliburton |
| 3,662,751 A | 5/1972 | Barkalow et al. |
| 3,669,108 A | 6/1972 | Sundblom et al. |
| 3,794,043 A | 2/1974 | McGinnis |
| 3,815,606 A | 6/1974 | Mazal |
| 3,834,383 A | 9/1974 | Weigl et al. |
| 3,933,171 A | 1/1976 | Hay |
| 4,041,943 A | 8/1977 | Miller |
| 4,077,404 A | 3/1978 | Elam |
| 4,166,458 A | 9/1979 | Harrigan |
| 4,226,233 A | 10/1980 | Kritzer |
| 4,259,951 A | 4/1981 | Chernack et al. |
| 4,298,023 A | 11/1981 | McGinnis |
| 4,316,458 A | 2/1982 | Hammerton-Fraser |
| 4,326,507 A | 4/1982 | Barkalow |
| 4,446,864 A | 5/1984 | Watson et al. |
| 4,449,526 A | 5/1984 | Elam |
| 4,533,137 A | 8/1985 | Sonne |
| 4,601,465 A | 7/1986 | Roy |

(Continued)

FOREIGN PATENT DOCUMENTS

| | | |
|---|---|---|
| CA | 668771 | 8/1963 |
| CA | 2077608 | 3/1993 |
| DE | 24 53 490 | 5/1975 |
| EP | 29352 | 5/1981 |
| EP | 0 139 363 | 5/1985 |

(Continued)

OTHER PUBLICATIONS

"Ventilators—Theory and Clinical Application," Dupuis, C.V. Mosby Co., St. Louis, MO @ 1986, pp. 447–448, 481. 496; ISBN 081614201.

(Continued)

Primary Examiner—Mital Patel
(74) Attorney, Agent, or Firm—Townsend and Townsend and Crew LLP

(57) ABSTRACT

A method for administering a drug to a patient comprises coupling a valve system to the patient's airway. The valve system is configured to prevent or impede respiratory gases from flowing into the lungs for at least some time such that the intrathoracic pressure is less than atmospheric pressure. A drug is introduced into the patient, and the intrathoracic pressure is lowered using the valve system to cause blood to flow into the thorax and thereby increasing vital organ perfusion to enhance the circulation of the drug.

19 Claims, 4 Drawing Sheets

U.S. PATENT DOCUMENTS

| | | |
|---|---|---|
| 4,881,527 A | 11/1989 | Lerman |
| 4,928,674 A | 5/1990 | Halperin et al. |
| 5,050,593 A | 9/1991 | Poon |
| 5,109,840 A | 5/1992 | Daleiden |
| 5,150,291 A | 9/1992 | Cummings et al. |
| 5,163,424 A | 11/1992 | Kohnke |
| 5,193,544 A | 3/1993 | Jaffe |
| 5,235,970 A | 8/1993 | Augustine |
| 5,295,481 A | 3/1994 | Geeham |
| 5,301,667 A | 4/1994 | McGrail et al. |
| 5,305,743 A | 4/1994 | Brain |
| 5,355,879 A | 10/1994 | Brain |
| 5,359,998 A | 11/1994 | Lloyd |
| 5,377,671 A | 1/1995 | Biondi et al. |
| 5,392,774 A | 2/1995 | Sato |
| 3,191,596 A | 6/1995 | Bird et al. |
| 5,454,779 A | 10/1995 | Lurie et al. |
| 5,551,420 A | 9/1996 | Lurie et al. |
| 5,588,422 A | 12/1996 | Lurie et al. |
| 5,645,522 A | 7/1997 | Lurie et al. |
| 5,692,498 A | 12/1997 | Lurie et al. |
| 5,730,122 A | 3/1998 | Lurie |
| 5,743,864 A | 4/1998 | Baldwin, II |
| 5,927,273 A | 7/1999 | Federowicz et al. |
| 6,062,219 A | 5/2000 | Lurie et al. |
| 6,155,257 A | 12/2000 | Lurie et al. |
| 6,176,237 B1 | 1/2001 | Wunderlich et al. |
| 6,374,827 B1 | 4/2002 | Bowden et al. |
| 6,463,327 B1 | 10/2002 | Lurie et al. |
| 6,776,156 B2 * | 8/2004 | Lurie et al. ............ 128/202.28 |

FOREIGN PATENT DOCUMENTS

| | | |
|---|---|---|
| EP | 0 245 142 | 11/1987 |
| EP | 0 367 285 | 5/1990 |
| EP | 0 411 714 A1 | 2/1991 |
| EP | 0 509 773 A1 | 4/1992 |
| GB | 1465127 | 2/1977 |
| GB | 2139099 | 11/1984 |
| WO | WO90/05518 | 5/1990 |
| WO | WO93/21982 | 11/1993 |
| WO | WO95/13108 | 5/1995 |
| WO | WO95/28193 | 10/1995 |
| WO | WO96/28215 | 9/1996 |

OTHER PUBLICATIONS

Directions for Use Ambu ® CardioPump™, pp. 1–8.

Cohen et al. (1992) "Active compression–decompression resuscitation: A novel method of cardiopulmonary resuscitation." *American Heart Journal* 124 (5): 1145–1150.

Cohen et al. (1992) "Active Compression–Decompression A New Method of Cardiopulmonary Resuscitation." *Jama* 267 (21): 2916–2923.

Linder et al. (1993) "Effects of Active Compression–Decompression Resuscitation on Myocardial and Cerebral Resuscitation Blood Flow in Pigs." *Circulation* 88 (3): 1254–1263.

Lurie et al. (1995) "Regulated to Death: The Matter of Informed Consent for Human Experimentation in Emergency Resuscitation Research." *PACE* 18: 1443–1447.

Mushin W.W. et al., "Automatic Ventilation of the Lungs—The Lewis–Leigh Inflating Valve," *Blackwell Scientific*, Oxford, GB, p. 838.

* cited by examiner

SYSTEMS AND METHODS TO FACILITATE THE DELIVERY OF DRUGS

CROSS REFERENCE TO RELATED APPLICATION

This application is a continuation of U.S. patent application Ser. No. 09/967,029, entitled "SYSTEMS AND METHODS TO FACILITATE THE DELIVERY OF DRUGS," filed Sep. 28, 2001 now U.S. Pat. No. 6,776,156 by Keith Lurie and Wolfgang Voelckel, the entire disclosure of which is incorporated herein by reference for all purposes.

BACKGROUND OF THE INVENTION

This invention relates generally to the field of drug delivery, and in particular to enhancing drug efficacy and reducing drug toxicity. More specifically, the invention relates to the drawing of blood into the thorax to increase vital organ perfusion to facilitate drug delivery.

Efficient drug delivery is critical factor in treating a variety of ailments. For example, drugs often need to be rapidly delivered to patients in cardiac arrest, or when suffering from diabetes, hypoglycemia, an anaphylactic reaction, seizures, asthma attacks, and the like. In some cases, drugs have short half lives and also need to be rapidly circulated. Hence, there is a need to rapidly distribute many drugs to the blood stream and vital organs. To increase the delivery rate of certain drugs, some have proposed simply increasing the concentration of the drug. However, the increased concentration may be toxic to the patient.

BRIEF SUMMARY OF THE INVENTION

In one embodiment, the invention provides a method for administering a drug to a patient. The method is designed to increase the efficacy of the drug, and in some cases to reduce the toxicity of the drug. According to the method, a valve system is coupled to the patient's airway. The valve system is configured to prevent or impede respiratory gases from flowing into the lungs for at least some time such that the intrathoracic pressure is artificially made to be less than atmospheric pressure. A drug is introduced into the patient, and the intrathoracic pressure is lowered in a repeating manner using the valve system to enhance blood to flow into the thorax. In this way, vital organ perfusion is increased to enhance the circulation of the drug. By increasing the circulation within the body with the valve system, the efficacy of the drug can be increased and less of the drug may be used to reduce the toxicity of the drug.

The method may be used to enhance drug efficacy and decrease toxicity for patients with low blood pressure, those in cardiac arrest, or those who need a rapid administration of a drug. For patients under cardiac arrest, the intrathoracic pressure may be reduced by using the valve system during standard CPR or by actively lifting the chest using a variety of CPR techniques, by electrically stimulating the respiratory and/or abdominal nerves or muscles, and the like while also preventing, restricting, or inhibiting respiratory gas flow into the lungs with the valve system for some period of time. The intrathoracic pressure may alternatively be reduced simply by breathing in while preventing or inhibiting respiratory gas flow to the lungs with the valve system. As another option, the intrathoracic pressure may be reduced by squeezing the chest and relaxing the chest with a chest caress while preventing or inhibiting airflow to the lungs with the valve system.

The valve system may be configured to prevent respiratory gases from entering the lungs until a certain threshold negative intrathoracic pressure is exceeded at which time gases may flow to the lungs. For example, the threshold negative pressure may be in the range from about 0 cm $H_2O$ to about 40 cm $H_2O$. At this point, the valve system permits respiratory gases to flow into the lungs. The valve system may optionally have an attached valve to create a range of positive end expiration pressures (PEEP) that typically occurs during compression of the patient's chest or when the patient exhales. This valve may be set to open when the positive intrathoracic pressure is in the range from about 0 cm $H_2O$ to about 20 cm $H_2O$.

The drug may be administered using a variety of techniques, For example, the drug may be introduced intravenously, through the patient's bone, through the patient's airway, including orally, nasally, and endobrochially, rectally, transdermally, and the like. As another option, the drug may be administered through a facial mask that is coupled to the patient's face or the valve system itself when coupled to the respiratory circuit.

A wide variety of drugs may be introduced into the patient. These include, for example, adrenaline or other supplemental drugs used to help maintain blood pressure when the patient is in cardiac arrest. Other examples include drugs that need to be rapidly delivered, such as glucose or adrenaline. Additional drugs include sodium bicarbonate, oxygen, steroids, vasopressor drugs, anti-arrhythmic drugs, anesthetics, anti-seizure medicines, and cooling solutions to cool the brain during cardiac arrest.

DETAILED DESCRIPTION OF THE INVENTION

Figure 1:
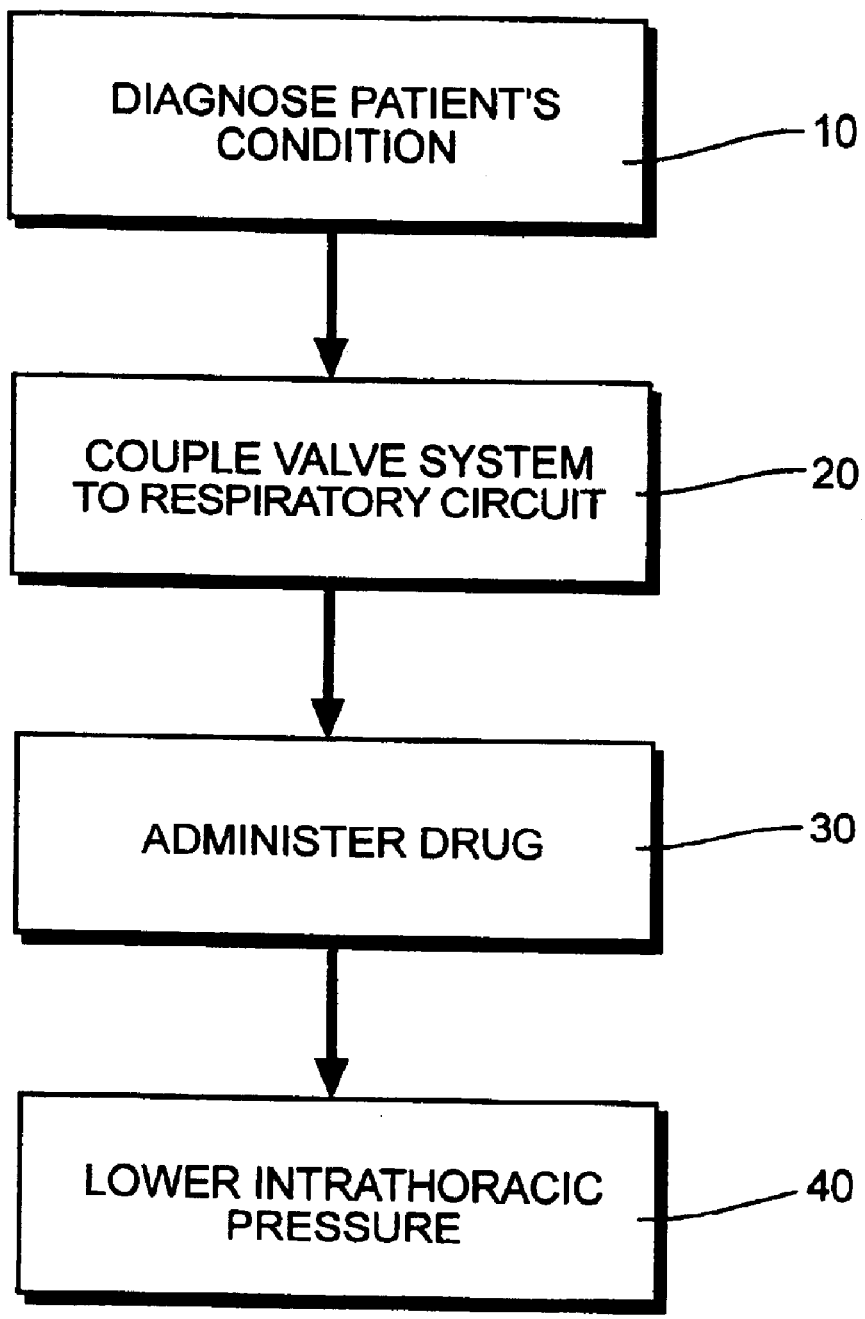
FIG. 1 is a flow chart illustrating a method for delivering a drug according to the invention.

The invention provides various methods and systems that are designed to enhance the drug efficacy and decrease drug toxicity for patients receiving one or more drugs. Such techniques may be used with patients having very low blood pressure, patients in cardiac arrest undergoing CPR, and patients who need a rapid administration of a drug with a normal blood pressure, among others.

The invention may be implemented by enhancing the negative intrathoracic pressure within the patient's chest to in turn enhance blood flow to the thorax to facilitate circulation of the drug throughout the blood stream and to the vital organs. This may be accomplished by preventing or impeding the flow of respiratory gases to the lungs under a variety of conditions, such as when performing CPR, when causing the respiratory or abdominal muscles to contract, when actively breathing, and the like. To prevent or impede respiratory gases from flowing to the lungs, a variety of impeding or preventing mechanisms may be used, including those described in U.S. Pat. Nos. 5,551,420; 5,692,498; 6,062,219; 5,730,122; 6,155,257; 6,234,916 and 6,224,562 and U.S. patent application Ser. No. 09/966,945 filed on the same date as the present application the complete disclosures of which are herein incorporated by reference.

For the patient in cardiac arrest, one way to augment the negative intrathoracic pressure is by placing such a valve system in the respiratory circuit. The resistance to the inflow of respiratory gases may be set between about 0 cm $H_2O$ and about 40 cm $H_2O$ and may be variable or fixed, based upon physiological parameters that could be measured simultaneously, including end tidal $CO_2$, blood pressure, $O_2$ saturation, body temperature, respiratory rate and the like. As described above, the valve may be configured to decrease intrathoracic pressures relative to atmosphere pressures and extrathoracic pressures, during the performance of any kind of CPR. Its use results in a greater vacuum in the thorax relative to the rest of the body during the decompression phase of CPR. This forces more blood back to the chest, thereby increasing blood available for the next compression. This results in a greater organ perfusion. Thus, rather than requiring a large amount of exogenous drug, such as, for example, adrenaline to help maintain the blood pressure, lower amounts of supplemental drug(s) are needed. Hence, the drug effect is more rapid and more prolonged with the valve system. In addition, the valve system reduces the potential toxicity of such types of drugs. For example, too much adrenaline is toxic to the heart. Using a lower concentration but getting a booster effect from the valve system would therefore be of benefit. The drugs can be delivered intravenously, through the bone (intraosseous), through the airway (orally, nasally, endobrochially), rectally, and transdermally. In essence, given the increased perfusion afforded by the valve system, drugs are circulated more rapidly to target sites and target organs. The valve system may be used with a variety of techniques including standard manual CPR, ACD CPR, vest CPR, phrenic nerve stimulator, and other compression devices used to perform CPR.

For patients with low blood pressure, inhalation may be prevented until a negative intrathoracic pressure in the range from about 4 cm $H_2O$ to about 20 cm $H_2O$ is achieved to cause a vacuum in the thorax relative to the rest of the body. A phrenic nerve stimulator or chest caress device that causes a decrease in intrathoracic pressure could also be used. This draws more blood back into the chest, resulting in a greater overall cardiac output. Combining the use of the valve system with drugs results in drug availability for target organs and may cause greater effectiveness of a given concentration of drug, the half life which may be dependent upon time in the body. Thus, the maximum effect and duration of effect are enhanced using the valve system. Similarly, patients with low blood pressure secondary to vaso-vagal syncope could inhale through the valve system, increasing their blood pressure and increasing the circulation of drugs administered in a number of ways to help treat this problem. Patients with seizure disorders could similarly inhale anti-seizure medication which could more rapidly be delivered to the brain.

The invention may also be used for patients who need the rapid administration of a drug. For those patients who are not necessarily in shock, such as, for example, those with diabetes and hypoglycemia, asthma, or those suffering from an anaphylactic reaction, inhalation through the valve system with simultaneous delivery of either glucose, or adrenaline, respectively, produces a more rapid onset of action of such drug effects. Oxygen will also circulate more rapidly. Thus, this invention may have widespread application as a means to enhance and facilitate the delivery of a medicinal agent(s).

Drugs which have toxicity can be used in lower concentrations. Drugs that are expensive but with a short half life will circulate more rapidly. This approach could be approach could be applied to vasopressor drugs, anti-arrhythmic drugs, anesthetics, cooling solutions to cool the brain during cardiac arrest, and the like. It can also be used to more rapidly clear toxic metabolic byproducts.

Drugs may be administered via the valve system or through a face mask valve to which the valve system is coupled, from an administration site or reservoir. If drugs, or compounds like glucose, sodium bicarbonate, oxygen, or steroids, can rapidly be absorbed via the pulmonary capillary vessels, then this approach may lead to a rapid delivery and onset of action for these agents.

Referring now to FIG. 1, one method for administering a drug will be described. In step 10, the patient is initially diagnosed to determine proper treatment. For example, the patient may be diagnosed as being in cardiac arrest, as having very low blood pressure, or simply need the rapid administration of a drug, such as when in shock, when suffering from diabetes and hypoglycemia, or suffering from an anaphylactic reaction.

In step 20, a valve system is coupled to the patient's respiratory circuit. This may be conveniently accomplished by use of a facial mask to which the valve system is coupled. Conveniently, the actuating pressure of the valve may be varied or set to a desired threshold pressure depending upon the diagnosis. The drug is administered to the patient as shown in step 30 using any of a variety of techniques as previously described.

The valve system is then used to lower the intrathoracic pressure as shown in step 40. In so doing, blood circulation is increased by creating a greater vacuum in the thorax relative to the rest of the body. This forces more blood back to the chest, thereby increasing blood circulation and vital organ perfusion during the next heart beat or when compressing the chest. The valve system may be used to lower the pressure by having the patient breathe in through the valve which prevents the flow of gases into the lungs and thereby lowers the intrathoracic pressure relative to atmospheric pressure. Other techniques that be used include actively lifting the chest using a variety of techniques, stimulating the respiratory and/or abdominal muscles and/or nerves, and the like.

Figure 2:
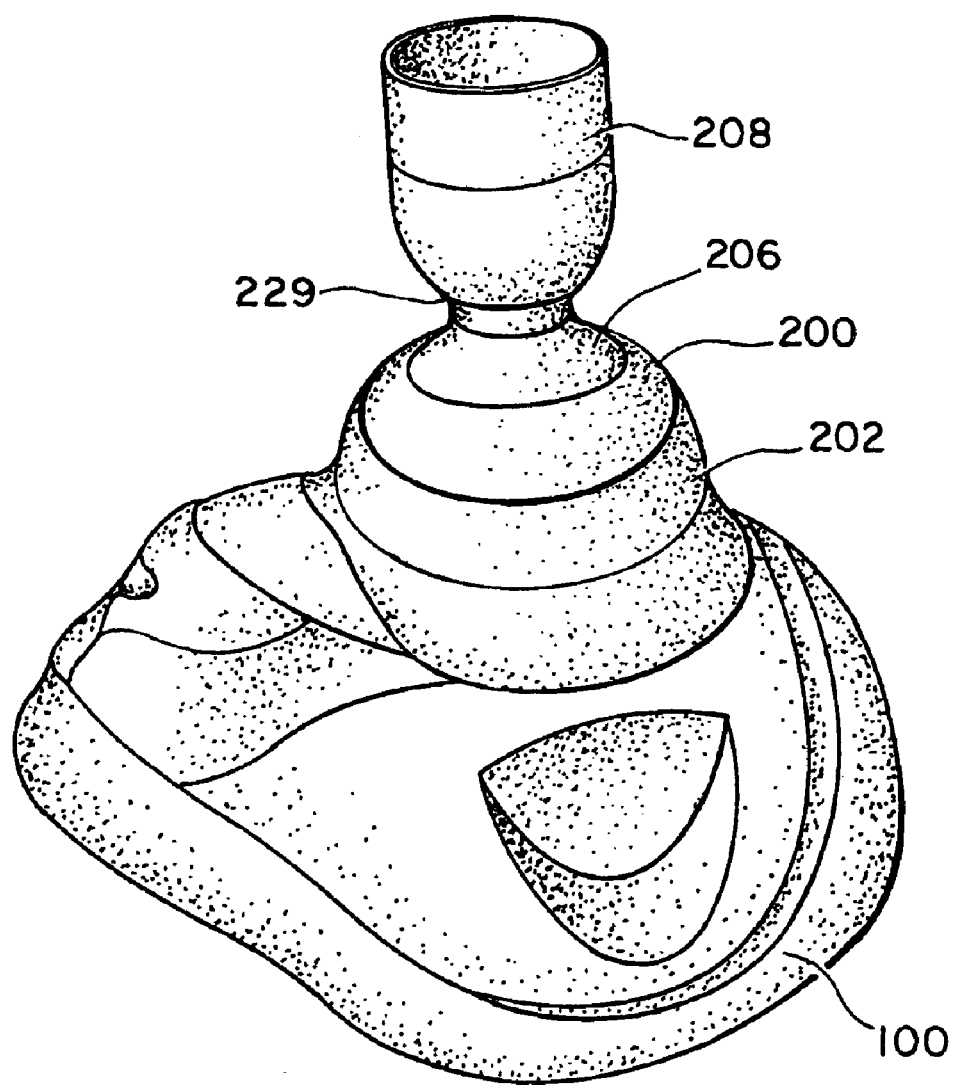
FIG. 2 is a perspective view of one embodiment of a facial mask and a valve system that is used to enhance the circulation of a drug according to the invention.
Figure 3:
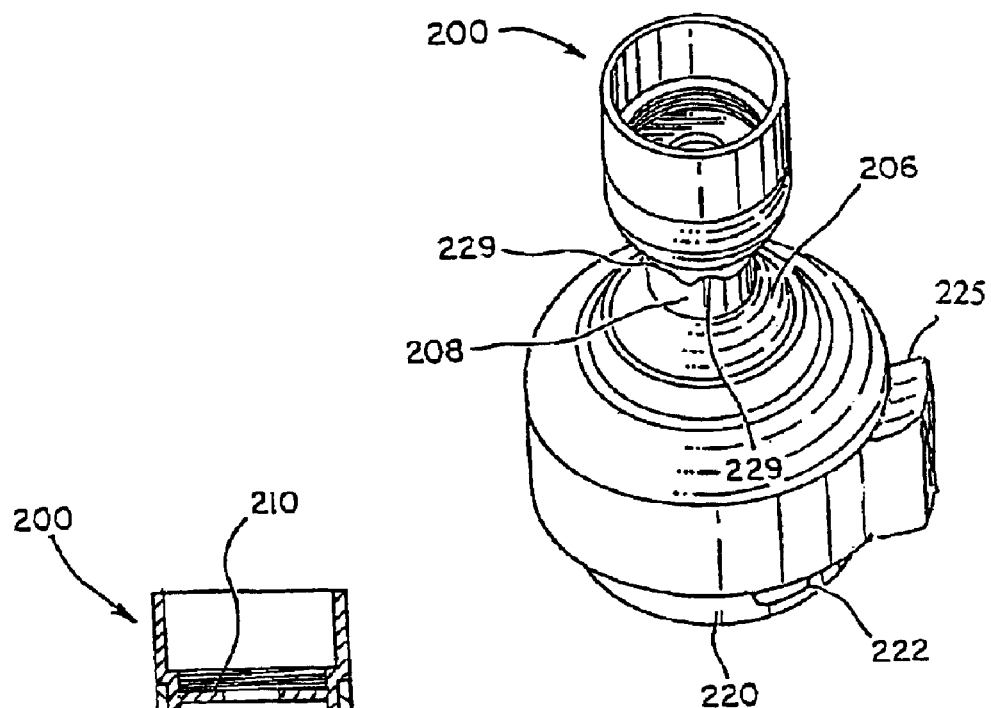
FIG. 3 is a perspective view of the valve system of FIG. 2.
Figure 4:
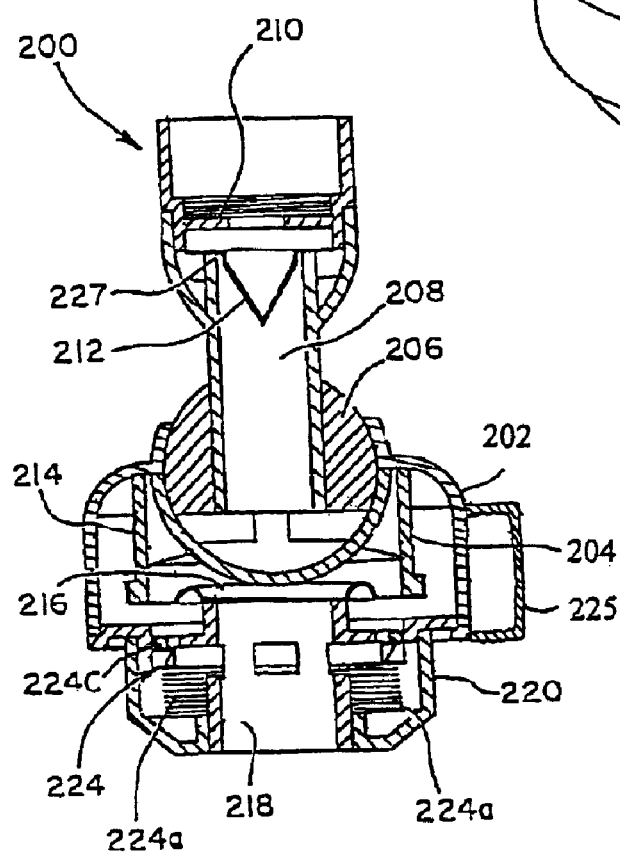
FIG. 4 is a cross sectional side view of the valve system of FIG. 3.
Figure 5:
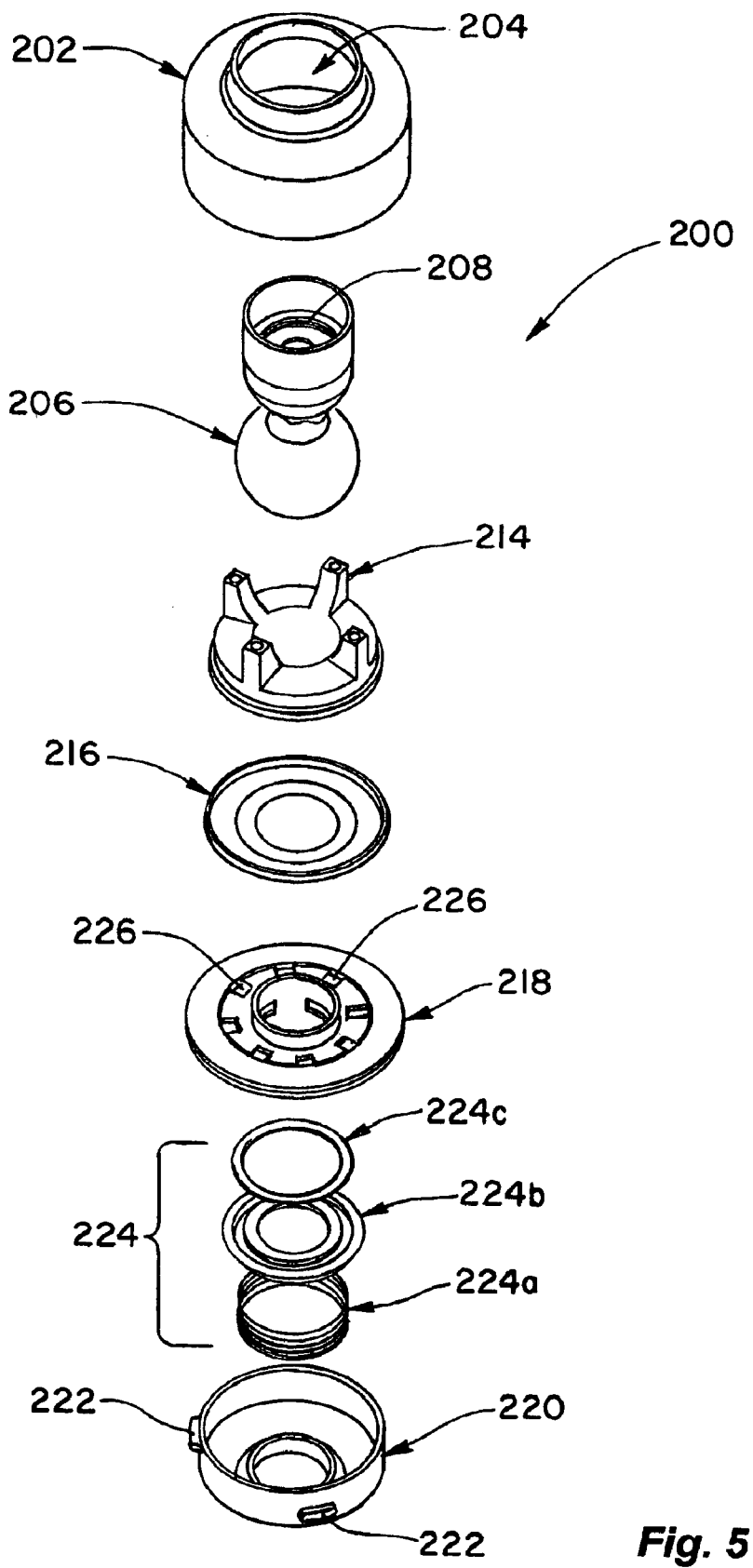
FIG. 5 is an exploded view of the valve system of FIG. 3.

FIG. 2 illustrates one embodiment of a facial mask 100 to which is coupled a valve system 200. Mask 100 is configured to be secured to a patient's face so as to cover the mouth and nose. Referring also to. FIGS. 3–5, valve system 200 will be described in greater detail. Valve .system 200 includes a valve housing 202 with a socket 204 into which a ball 206 of a ventilation tube 208 is received. In this way, ventilation tube 208 may rotate about a horizontal axis and pivot relative to a vertical axis. A respiratory source, such as a ventilation bag, may be coupled to tube 208 to assist in ventilation. Disposed in ventilation tube 208 is a filter 210 that is spaced above a duck bill valve 212. A diaphragm holder 214 that holds a diaphragm 216 is held within housing 202. Valve system 200 further includes a patient port 218 that is held in place by a second housing 220. Housing 220 conveniently includes tabs 222 to facilitate coupling of valve system 200 with facial mask 100. Also held within housing 220 is a check valve 224 that comprises a spring 224a, a ring member 224b, and an o-ring 224c. Spring 224a biases ring member 224b against patient port 218. Patient port 218 includes bypass openings 226 that are covered by o-ring 224c of check valve 224 until the pressure m patient port 218 reaches a threshold negative pressure to cause spring 224a to compress.

When the patient is actively ventilated, respiratory gases are forced through. ventilation tube 208. The gases flow through filter 210, through duck bill valve 212, and forces up diaphragm 214 to permit the gases to exit through port 218. Hence, at any time during the performance of CPR the patient may be ventilated simply by forcing the respiratory gases through tube 208.

During the compression phase of CPR, expired gases flow through port 218 and lift up diaphragm 214. The gases then flow through a passage 227 in ventilation tube 208 where they exit the system through openings 229 (see FIG. 16).

During the recovery or decompression phase of CPR where the patient's chest is actively lifted or allowed to expand, valve system 200 prevents respiratory gases from flowing into the lungs until a threshold of negative intrathoracic pressure level is exceeded. When this pressure level is exceeded, check valve 224 is pulled downward as springs 224a are compressed to permit respiratory gases to flow through openings 226 and to the patient's lungs by initially passing through tube 208 and duck bill valve 212. Valve 224 may be set to open when the negative intrathoracic pressure is in the range from about 0 cm $H_2O$ to about −40 cm $H_2O$, and more preferably from about −5 cm $H_2O$ to about −30 cm $H_2O$. Hence, the magnitude and duration of negative intrathoracic pressure may be enhanced during decompression of the patient's chest by use of valve system 200. Once the intrathoracic pressure falls below the threshold, recoil spring 224a again close check valve 224. In this way, circulation is increased to cause more blood to flow into the thorax and thereby increase vital organ perfusion to enhance the circulation of the drug.

Conveniently, a drug storage compartment 225 may be interfaced with or part of a fare mask system that includes the valve system. In this way, an appropriate drug may be rapidly accessed when needed.

In another aspect, the valve system may be coupled to an inhalation device, such as a nebulizer, aerosolizer, dry powder dispersion device or the like where the patient inhales from a mouthpiece to deliver a drug to the lungs. The valve system may be positioned within the airway, such as upstream of the mouthpiece, to regulate the flow of respiratory gases to the lungs as previously described. Such inhalation devices may be used to deliver medications, such as asthma medications, to the patient. The valve system may also be used to prevent gas flow to the lungs until the user generates sufficient energy to extract a drug from the inhalation device. In such cases, the threshold valve may be set to open up to about −60 cm $H_2O$. In this way, the valve system may be used to increase circulation of the drug as well as to create sufficient energy to extract the drug.

The invention has now been described in detail for purposes of clarity and understanding. However, it will be appreciated that certain changes and modifications may be practiced within the scope of the appended claims.

What is claimed is:

1. A method for administering a drug to a patient suffering from hypotension, the method comprising:
    coupling a valve system to the patient's airway, wherein the valve system is configured to prevent or impede respiratory gases from flowing into the lungs for at least some time such that the intrathoracic pressure is less than atmospheric pressure;
    introducing a hynotension-treatment drug into the patient; and
    lowering the intrathoracic pressure using the valve system to cause blood to flow into the thorax and thereby increasing vital organ perfusion to enhance the circulation of the drug.

2. A method as in claim 1, wherein the intrathoracic pressure is reduced by spontaneous breathing by the patient while preventing or inhibiting respiratory gas flow to the lungs with the valve system.

3. A method as in claim 1, wherein the valve system is configured to prevent respiratory gases from entering the lungs until a threshold negative intrathoracic pressure in the range from about 0 cm $H_2O$ to about 40 cm $H_2O$ is exceeded.

4. A method as in claim 1, wherein the drug is administered through a facial mask or the valve system.

5. A method as in claim 1, wherein the valve system is configured to prevent respiratory gases from exiting the patient's lungs until a positive end expiratory pressure in the range from about 0 cm $H_2O$ to about 20 cm $H_2O$ is exceeded.

6. A method as in claim 1, wherein the valve system is coupled to a facial mask that is placed over the mouth and nose, and further comprising removing the drug from a drug storage compartment of the facial mask.

7. A method as in claim 1, wherein the valve system is coupled to an inhalation device that includes the drug, and further comprising inhaling from the inhalation device to administer the drug.

8. A method for administering a drug to a patient suffering from heart failure, the method comprising:
    coupling a valve system to the patient's airway, wherein the valve system is configured to prevent or impede respiratory gases from flowing into the lungs for at least some time such that the intrathoracic pressure is less than atmospheric pressure until a magnitude of a threshold negative intrathoracic pressure in the range from about 0 cm $H_2O$ to about 40 cm $H_2O$ is exceeded;
    introducing a heart-failure-treatment drug into the patient; and
    lowering the intrathoracic pressure by spontaneous breathing of the patient while preventing or inhibiting respiratory gas flow to the lungs with the valve system to cause blood to flow into the thorax and thereby increasing vital organ perfusion to enhance the circulation of the drug.

9. A method as in claim 8 wherein the drug is administered through a facial mask or the valve system.

10. A method as in claim 8 wherein the valve system is configured to prevent respiratory gases from exiting the patient's lungs until a positive end expiratory pressure in the range from about 0 cm $H_2O$ to about 20 cm $H_2O$ is exceeded.

11. A method as in claim 8 wherein the valve system is coupled to a facial mask that is placed over the mouth and nose, and further comprising removing the drug from a drug storage compartment of the facial mask.

12. A method as in claim 8 the valve system is coupled to an inhalation device that includes the drug, and further comprising inhaling from the inhalation device to administer the drug.

13. A method for administering a drug to a patient, the method comprising:
    coupling a valve system to the patient's airway, wherein the valve system is configured to prevent or impede respiratory gases from flowing into the lungs for at least some time such that the intrathoracic pressure is less than atmospheric pressure;
    introducing a drug into the patient;
    measuring a physiological parameter of the patient; and
    lowering the intrathoracic pressure to a value based on the measured physiological parameter using the valve system to cause blood to flow into the thorax and thereby increasing vital organ perfusion to enhance the circulation of the drug.

14. A method as in claim 13 wherein the physiological parameter is selected from the group consisting of an end tidal $CO_2$ value, a blood-pressure value, an $O_2$ saturation value, a body-temperature value, and a respiratory-rate value.

15. A method as in claim 13 wherein the intrathoracic pressure is reduced by spontaneous breathing by the patient while preventing or inhibiting respiratory gas flow to the lungs with the valve system.

16. A method as in claim 13 wherein the drug is administered through a facial mask or the valve system.

17. A method as in claim 13 wherein the drugs are selected from a group consisting of glucose, sodium bicarbonate, oxygen, steroids, vasopressor drugs, anti-arrhythmic drugs, anti-seizure, anti-asthma, anesthetics, and cooling solutions to cool the brain during cardiac arrest.

18. A method as in claim 13 wherein the valve system is coupled to a facial mask that is placed over the mouth and nose, and further comprising removing the drug from a drug storage compartment of the facial mask.

19. A method as in claim 13 wherein the valve system is coupled to an inhalation device that includes the drug, and further comprising inhaling from the inhalation device to administer the drug.

* * * * *